US007814679B2

(12) United States Patent
Yan et al.

(10) Patent No.: US 7,814,679 B2
(45) Date of Patent: *Oct. 19, 2010

(54) METHOD OF FABRICATING ABRASIVE HAVING SLIDING AND GRINDING EFFECTS

(75) Inventors: Biing-Hwa Yan, Kaohsiung (TW); Feng-Che Tsai, Changhua (TW); Li-Wen Sun, Gangshan Township, Kaohsiung County (TW)

(73) Assignee: National Central University, Taoyuan County (TW)

( * ) Notice: Subject to any disclaimer, the term of this patent is extended or adjusted under 35 U.S.C. 154(b) by 281 days.

This patent is subject to a terminal disclaimer.

(21) Appl. No.: 12/081,744

(22) Filed: Apr. 21, 2008

(65) Prior Publication Data

US 2008/0271380 A1 Nov. 6, 2008

(30) Foreign Application Priority Data

May 3, 2007 (TW) .............................. 96115763 A

(51) Int. Cl.
F26B 3/08 (2006.01)
B24D 3/02 (2006.01)
C09C 1/68 (2006.01)
C09K 3/14 (2006.01)
B24B 1/00 (2006.01)
C04B 33/32 (2006.01)
C04B 35/64 (2006.01)

(52) U.S. Cl. ............................ 34/373; 51/307; 51/308; 51/309; 34/372; 264/661

(58) Field of Classification Search ........... 51/307–309; 34/372–373, 381; 264/661
See application file for complete search history.

(56) References Cited

U.S. PATENT DOCUMENTS

| 2,636,555 | A | * | 4/1953 | Klepetko et al. ............. 159/4.1 |
| 2,833,345 | A | * | 5/1958 | Van der Pyl ............... 159/4.07 |
| 3,274,642 | A | * | 9/1966 | Cramer .......................... 425/6 |
| 3,618,655 | A | * | 11/1971 | Lockwood .................. 159/4.02 |
| 4,238,429 | A | * | 12/1980 | Sasaki et al. ................... 264/13 |
| 5,078,793 | A | * | 1/1992 | Caton ......................... 106/417 |
| 5,227,017 | A | * | 7/1993 | Tanaka et al. .............. 159/4.01 |
| 6,551,366 | B1 | * | 4/2003 | D'Souza et al. ............... 51/309 |
| 6,560,897 | B2 | * | 5/2003 | Chickering et al. ........... 34/577 |
| 7,229,985 | B2 | * | 6/2007 | Ishikura et al. ........ 514/212.06 |
| 2006/0006589 | A1 | * | 1/2006 | Canova et al. ............. 264/661 |

FOREIGN PATENT DOCUMENTS

WO WO 03/055886 * 7/2003

OTHER PUBLICATIONS

Perry's Chemical Engineers' Handbook, 7th Edition, 1997, pp. 20-80 to 20-81 [no month].*

* cited by examiner

Primary Examiner—Anthony J Green
Assistant Examiner—Pegah Parvini
(74) Attorney, Agent, or Firm—Jackson IPG PLLC; Demian K. Jackson

(57) ABSTRACT

An abrasive is fabricated to obtain sliding and grinding effects. In the abrasive, grinding particles are wrapped by a wrapping material. Various sizes and shapes of molds and micro components can be finely polished to obtain mirror-grade surfaces.

7 Claims, 5 Drawing Sheets

METHOD OF FABRICATING ABRASIVE HAVING SLIDING AND GRINDING EFFECTS

FIELD OF THE INVENTION

The present invention relates to fabricating an abrasive; more particularly, relates to wrapping grinding particles with a lubricant wrapping material through atomization to obtain a compound abrasive having sliding and grinding effects.

DESCRIPTION OF THE RELATED ARTS

A traditional polish with an abrasive obtains a fine surface, yet the abrasive used is made of a single material and so polishing result obtained is limited. The result is affected by a working pressure, a particle diameter and a particle shape. In a general polish to a work piece, the abrasive transmits power and the power transmitted is obtained by an interface stress and an interaction between the abrasive and the work piece. The greater the power transmitted is, the greater the amount removed from a surface of the work piece is. The value of the interface stress relates to a horizontal friction between the abrasive and the work piece. When a very high pressure is put on the abrasive, a reaction force (friction force) is generated by the abrasive on the work piece and a carving force is thus obtained between the abrasive and the work piece on contacting with each other.

When the reaction force generated by the abrasive is greater, the abrasive has a greater carving force toward the surface of the working piece. The carving force of the abrasive toward the working piece not only relates to the roughness of the surface of the working piece and the reaction force owing to the pressure, but also closely relates to hardness, diameters and shapes of particles of the abrasive. Hence, it is quite common that, for reducing the carving force of the abrasive toward the working piece, the pressure is lowered or the diameters of particles of the abrasive are reduced. But often is the result that the carving force becomes too small or the price of the abrasive becomes too high owing to the high cost for producing the small particles. In a word, it is hard to obtain a low cost and a mirror-like surface at the same time.

The methods of fabricating abrasive particles are many. Different methods obtain different shapes, sizes, diameters, distributions and micro-constitutions of particles. However, the particles are made of the same material. In the same environment, polishing methods using the traditional abrasive particles can not obtain a mirror-like surface on the work piece. Hence, the prior arts do not fulfill all users' requests on actual use.

SUMMARY OF THE INVENTION

The main purpose of the present invention is to grind and polish various sizes and shapes of molds and micro components with a compound abrasive having sliding and grinding effects to obtain mirror-grade surfaces.

To achieve the above purpose, the present invention is a method of fabricating an abrasive having sliding and grinding effects, comprising steps of: (a) melting a wrapping material under a high temperature to be uniformly mixed with grinding particles; (b) spraying the mixture of the grinding particles and the wrapping material into a compound abrasive collecting chamber by using a high-pressure gas to obtain micro-balls of the grinding particles and the wrapping material; and, (c) inputting a low-temperature gas into the compound abrasive collecting chamber to instantly solidify the micro-balls owing to a temperature difference to obtain a compound abrasive, where the compound abrasive has sliding and grinding effects with the grinding particles wrapped by the wrapping material. Accordingly, a novel method of fabricating an abrasive having sliding and grinding effects is obtained.

BRIEF DESCRIPTIONS OF THE DRAWINGS

The present invention will be better understood from the following detailed description of the preferred embodiment according to the present invention, taken in conjunction with the accompanying drawings, in which FIG. 1 is the flow view showing the preferred embodiment according to the present invention;

DESCRIPTION OF THE PREFERRED EMBODIMENTS

The following description of the preferred embodiment is provided to understand the features and the structures of the present invention.

Figure 1:
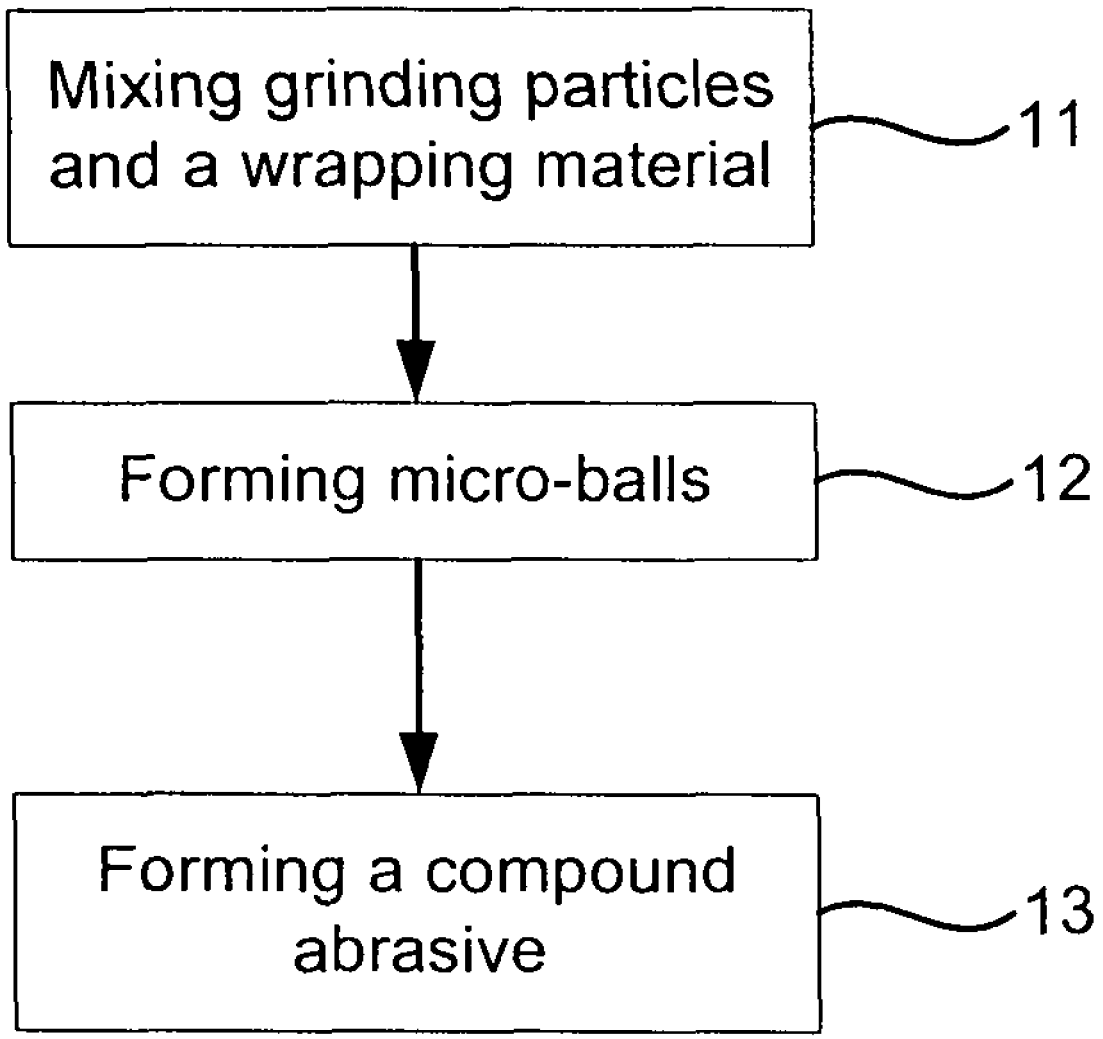
Figure 2:
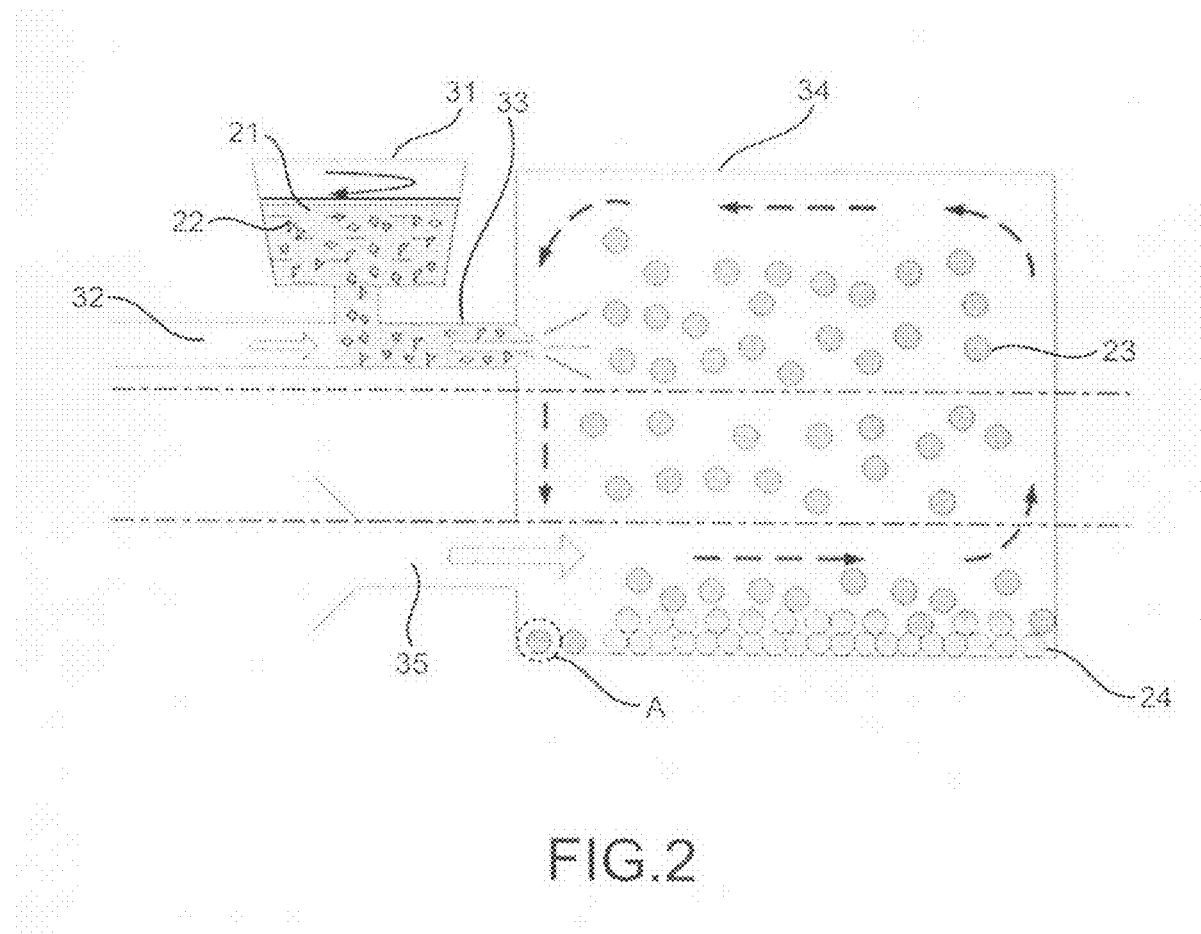
FIG. 2 is the view showing fabricating the compound abrasive.
Figure 3:
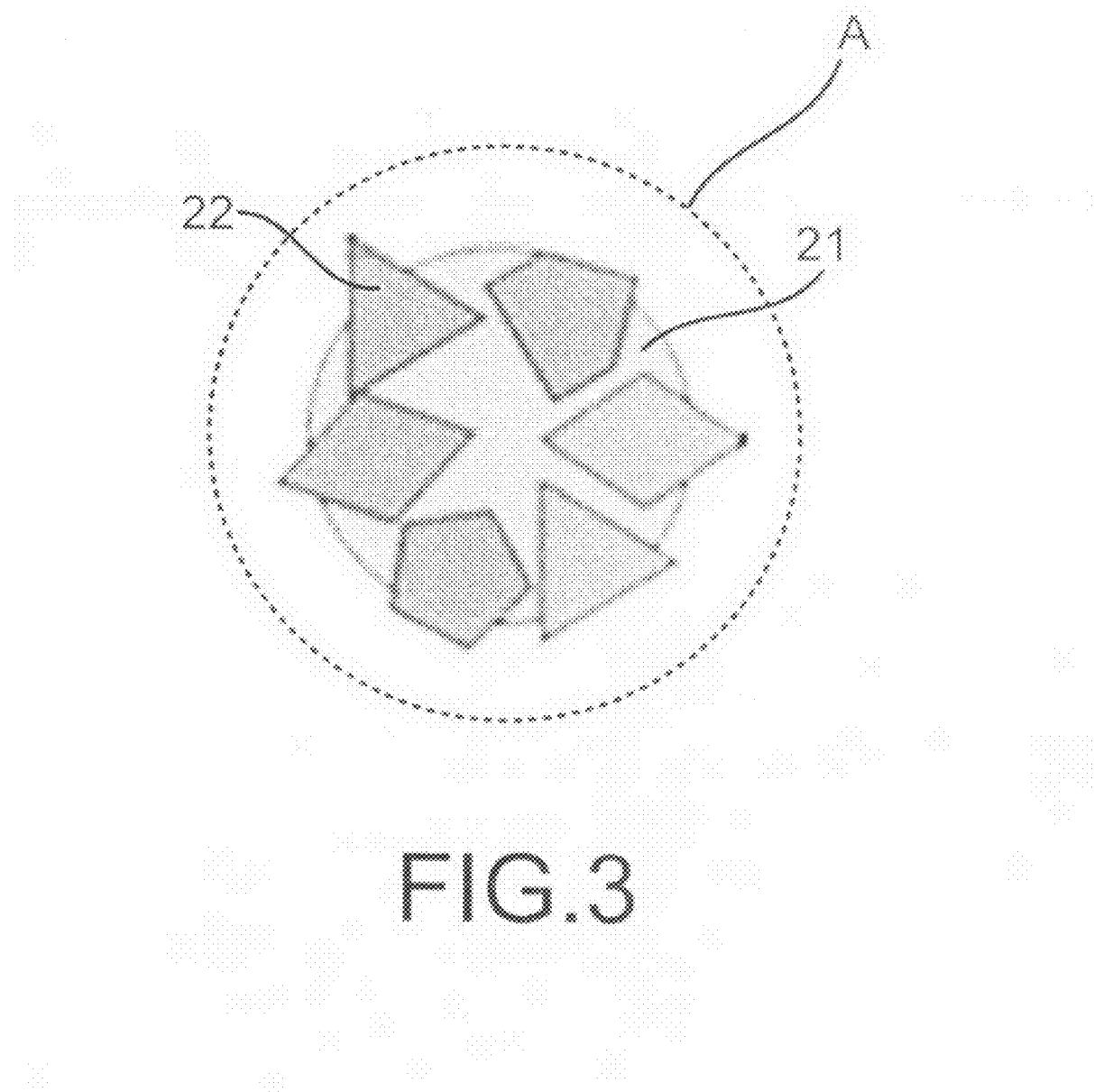
FIG. 3 is the enlarged view showing the 'A' in FIG. 2.

Please refer to FIG. 1 to FIG. 3, which are a flow view showing a preferred embodiment according to the present invention; a view showing fabricating a compound abrasive; and an enlarged view showing 'A' in FIG. 2. As shown in the figures, the present invention is a method of fabricating an abrasive having sliding and grinding effects, comprising the following steps:

(a) Mixing grinding particles and a wrapping material 11: A wrapping material 21 and grinding particles 22 are mixed in a compound abrasive mixing bucket 31 at a volume ratio to be heated to totally melt the wrapping material; and, the melted wrapping material 21 is uniformly mixed with the grinding particles 22 by stirring. Therein, the wrapping material 21 is a wax, an animal oil, a plant oil or a hot plastic resin; the grinding particle is an oxide, a polymer or an element; the grinding particle is further a diamond, SiC, polycrystalline cubic boron nitride (PCBN) or aluminum oxide ($Al_2O_3$); the grinding particle has a diameter between 1 and 100 micrometers (μm); and, the grinding particles are harder than a work piece to be polished.

(b) Forming micro-balls 12: A high-pressure gas is inputted through a high-pressure gas supplying pipe 32 to spray the wrapping material 21 with the grinding particles 22 through a micro-pore of a nebulizing nozzle 33. Thus, micro-balls 23 comprising the grinding particles 22 and the wrapping material 21 are formed to enter a compound abrasive collecting chamber 34. Therein, the high-pressure gas has a pressure between 1 and 100 mega-pascals (MPa).

(c) Forming a compound abrasive 13: A second gas (i.e., a low temperature gas) is inputted into the compound abrasive collecting chamber 34 through a low-temperature gas supplying pipe 35. Thus, a low-temperature environment is formed to solidify the micro-balls 23 instantly. Hence, a compound abrasive 24 having sliding and grinding effects is formed.

Accordingly, a lubricant material is wrapped on the grinding particles through a atomization to reduce a reaction force of the grinding particles 22. Not only a lubrication effect of the compound abrasive 24 is improved, but also sliding and grinding effects of the compound abrasive 24 are enhanced. The present invention is suitable to grind and polish various sizes and shapes of molds and micro components, like microinjection molds, micro-channels for biomedical detections, micro electro-mechanical systems and all kinds of micro-machining, to obtain a mirror-grade surface.

On using the present invention, a compound abrasive 24 having sliding and grinding effects is made of a wrapping material 21 and grinding particles 22. For example, a wax is taken as the wrapping material 21, and SiC as the grinding particles 14. The wrapping material 21 is melted through heating to be uniformly mixed with the grinding particles 22 by stirring at a volume ratio of 1:1. A first gas of 100MPa (i.e., a high-pressure gas) is used to spray the wrapping material 21 and the grinding particles 22 from a nebulizing nozzle 33 of 0.5 millimeter (mm). The high-temperature wrapping material 21 is then covered on the grinding particles to obtain 0.02mm micro-balls 23. The micro-balls 23 are sent into a compound abrasive collecting chamber 34, which is already filled with a low- temperature gas at 5 to 10 Celsius degrees. Thus, the micro-balls 23 are solidified instantly owing to the temperature difference and the compound abrasive 24 is obtained at the same time.

Figure 4:
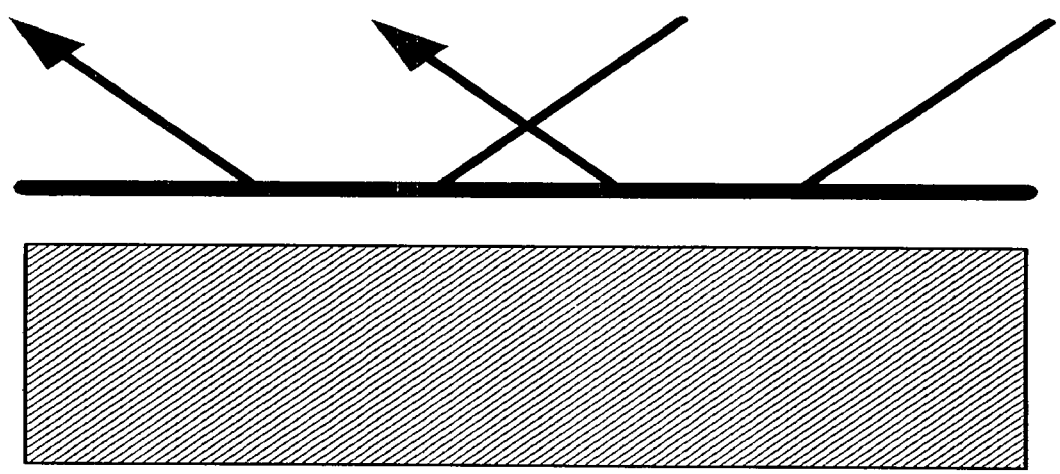
FIG. 4 is the view showing polishing with sliding.
Figure 5:
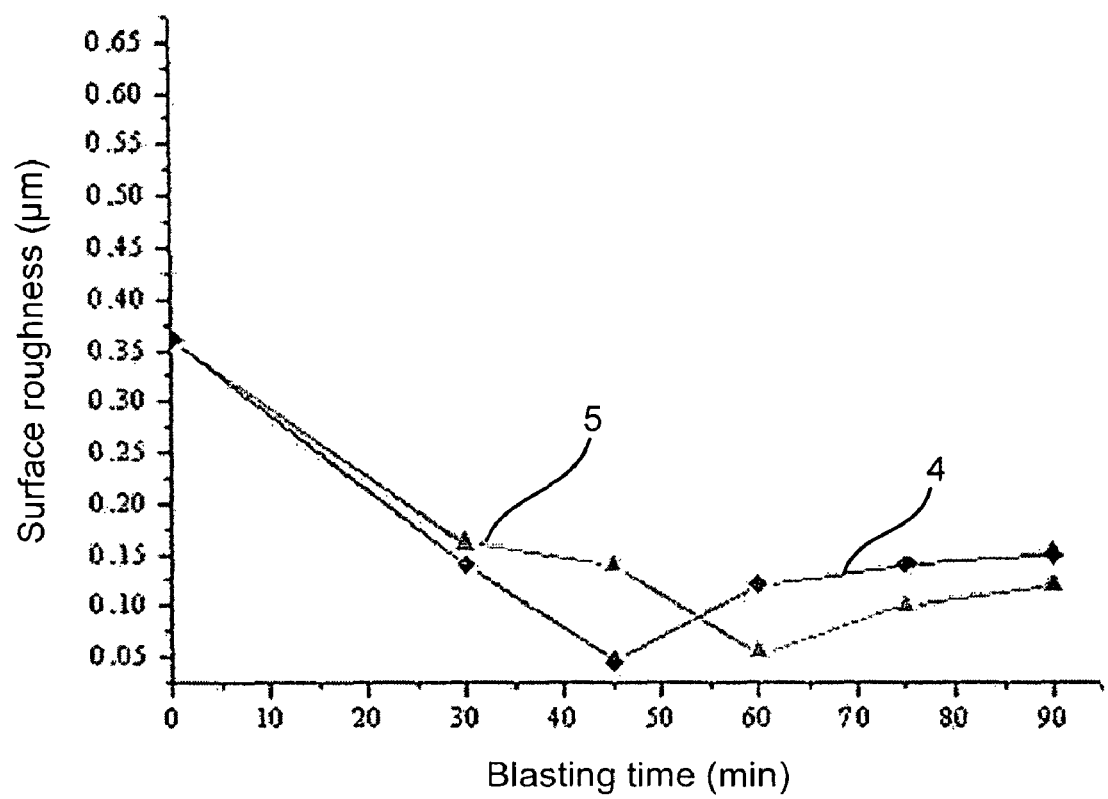
FIG. 5 is the view showing the comparison between the polishes.

Please refer to FIG. 4 and FIG. 5, which are views showing polishing with sliding; and a comparison between two polishes. As shown in the figures, polishing path of a compound abrasive according to the present invention shows that sliding and grinding effects of grinding particles are greatly enhanced on a surface of a work piece. By comparing a curve for the compound abrasive 4 and a curve for traditional grinding particles 5 with the same surface roughness of 0.36 mm, the compound abrasive 4 reduces its polishing time to an extent of 25% by comparing to that of the traditional grinding particles 5. It shows that the compound abrasive 4 according to the present invention has a greatly improvement on polishing. Thus, with such a great polishing improvement, a work piece can be ground by the compound abrasive to obtain a mirror-grade surface.

To sum up, the present invention is a method of fabricating an abrasive having sliding and grinding effects, where various sizes and shapes of molds and micro components are finely ground and polished to obtain mirror-grade surfaces.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of fabricating an abrasive having sliding and grinding effects, comprising steps of:
   (a) melting a wrapping material under a temperature to be uniformly mixed with grinding particles by stirring in a compound abrasive mixing bucket at a volume ratio of said grinding particles to said wrapping material;
   (b) spraying said mixture of said grinding particles and said melted wrapping material into a compound abrasive collecting chamber from a micro-pore nebulizing nozzle by using a high pressure gas, to obtain micro-balls each comprising said grinding particles and said wrapping material; and
   (c) inputting a low temperature gas into said compound abrasive collecting chamber at a temperature selected to instantly solidify said micro-balls to obtain a compound abrasive,
   wherein the low temperature gas is input at a temperature of 5 to 10 Celsius.

2. The method according to claim 1, wherein said wrapping material is selected from a group consisting of a wax, an animal oil, a plant oil and a hot plastic resin.

3. The method according to claim 1, wherein said grinding particle is selected from a group consisting of an oxide, a polymer and an element.

4. The method according to claim 3, wherein said grinding particle is further selected from a group consisting of a diamond, SiC, polycrystalline cubic boron nitride (PCBN) and aluminum oxide ($Al_2O_3$).

5. The method according to claim 1, wherein said grinding particle has a diameter between 1 and 100 micro-meter (μm).

6. The method according to claim 1, wherein said high-pressure gas has a pressure between 1 and 100 mega-pascals (MPa).

7. The method according to claim 1, wherein said grinding particle has a hardness higher than a work piece to be polished.

* * * * *